United States Patent
Rosar et al.

(10) Patent No.: US 8,102,789 B2
(45) Date of Patent: Jan. 24, 2012

(54) SYSTEM AND METHOD FOR SYNCHRONOUS WIRELESS COMMUNICATION WITH A MEDICAL DEVICE

(75) Inventors: George C. Rosar, Minneapolis, MN (US); Gregory J. Haubrich, Champlin, MN (US); Javaid Masoud, Shoreview, MN (US); Charles S. Farlow, Waconia, MN (US)

(73) Assignee: Medtronic, Inc., Minneapolis, MN (US)

( * ) Notice: Subject to any disclaimer, the term of this patent is extended or adjusted under 35 U.S.C. 154(b) by 1791 days.

(21) Appl. No.: 11/321,184

(22) Filed: Dec. 29, 2005

(65) Prior Publication Data

US 2007/0153705 A1    Jul. 5, 2007

(51) Int. Cl.
G08C 17/00 (2006.01)
H04W 4/00 (2009.01)
H04B 7/212 (2006.01)

(52) U.S. Cl. .......................... 370/311; 370/329; 370/442
(58) Field of Classification Search .................. 370/431, 370/436, 442, 443, 463, 503, 310, 311, 328–330; 607/60

See application file for complete search history.

(56) References Cited

U.S. PATENT DOCUMENTS

| | | | |
|---|---|---|---|
| 5,350,407 A | 9/1994 | McClure et al. | |
| 5,350,411 A | 9/1994 | Ryan et al. | |
| 6,472,991 B1 | 10/2002 | Schulman et al. | |
| 6,644,321 B1 | 11/2003 | Behm | |
| 6,738,670 B1 | 5/2004 | Almendinger et al. | |
| 7,406,105 B2 * | 7/2008 | DelMain et al. | 370/519 |
| 7,532,585 B2 * | 5/2009 | Kim et al. | 370/254 |
| 7,860,557 B2 * | 12/2010 | Istvan et al. | 600/509 |
| 7,933,642 B2 * | 4/2011 | Istvan et al. | 600/509 |
| 2002/0198513 A1 | 12/2002 | Lebel et al. | |
| 2003/0114898 A1 | 6/2003 | Von Arx et al. | |
| 2005/0283198 A1 | 12/2005 | Haubrich et al. | |
| 2006/0136015 A1 | 6/2006 | Park et al. | |
| 2008/0255636 A1 * | 10/2008 | DelMain et al. | 607/60 |

OTHER PUBLICATIONS

International Search Report, PCTUS/2006/061943, Feb. 4, 2007, 6 Pages.
AMIS-52100 Receiver Sniff Mode™ (Application Note), undated.

* cited by examiner

*Primary Examiner* — Aung S Moe
*Assistant Examiner* — Kerri Rose
(74) *Attorney, Agent, or Firm* — Stephen W. Bauer; Michael J. Ostrom

(57) ABSTRACT

Constituents of a network of medical devices communicate according to a synchronous communication protocol. A constituent of the network is established as a conductor. Time slots are assigned to each constituent of the network other than the conductor. Information is communicated between the constituents of the network in the assigned time slots.

20 Claims, 8 Drawing Sheets

SYSTEM AND METHOD FOR SYNCHRONOUS WIRELESS COMMUNICATION WITH A MEDICAL DEVICE

CROSS-REFERENCE TO RELATED APPLICATION(S)

Reference is made to the following applications:

U.S. application Ser. No. 11/224,591 filed Sep. 12, 2005 for "SYSTEM AND METHOD FOR UNSCHEDULED WIRELESS COMMUNICATION WITH A MEDICAL DEVICE" by Quentin S. Denzene and George C. Rosar;

U.S. application Ser. No. 11/224,593 filed Sep. 12, 2005 for "SYSTEM AND METHOD FOR UNSCHEDULED WIRELESS COMMUNICATION WITH A MEDICAL DEVICE" by Gregory J. Haubrich, Len D. Twetan, David Peichel, Charles S. Dudding, George C. Rosar and Quentin S. Denzene;

U.S. application Ser. No. 11/224,594 filed Sep. 12, 2005 for "IMPLANTABLE MEDICAL DEVICE COMMUNICATION SYSTEM WITH MACRO AND MICRO SAMPLING INTERVALS" by Glenn Spital; and U.S. applicaton No. 11/224,595 filed Sep. 12, 2005 for "COMMUNICATION SYSTEM AND METHOD WITH PREAMBLE ENCODING FOR AN IMPLANTABLE MEDICAL DEVICE" by Gregory j. Haubrich, Javaid Masoud, George C. Rosar, Glenn Spital and Quentin S. Denzene.

BACKGROUND OF THE INVENTION

The present invention relates to wireless communication with medical devices such as implantable medical devices.

Medical devices, including implantable medical devices (IMDs) are now used to provide countless therapies and to monitor a wide variety of physiological events. With the increased uses of IMDs has also come the need for improved methods of communicating with and between IMDs.

Conventionally, communication with IMDs has been performed with magnetic field communication technology. Systems that employ this communication technology, however, are generally only capable of communicating over very short distances, on the order of a few inches. As a result, a magnetic head of a programmer (or other external device) must be located on or near the IMD for communication to occur. More recently, radio frequency (RF) communication systems have been developed for use with IMDs. RF communication provides a number of benefits over magnetic field communication systems, including much greater communication distances.

Because an IMD is surgically implanted within the body of a patient, battery life is one of the factors to be considered in the design of IMD communication systems. There is also an ongoing desire to enable more and more advanced communications between IMDs and other devices. Accordingly, there is a need for systems and methods to provide advanced communication capabilities while limiting the amount of time that the transceiver of an IMD stays active to conserve battery life.

BRIEF SUMMARY OF THE INVENTION

Medical devices in a network communicate with one another according to a synchronous communication protocol. A constituent of the network is established as a conductor. Time slots are assigned by the conductor for communication to occur. Information is communicated between the constituents of the network in the assigned time slots. The medical devices preserve battery life by limiting how often their transceivers need to operate or remain active.

DETAILED DESCRIPTION

Figure 1:
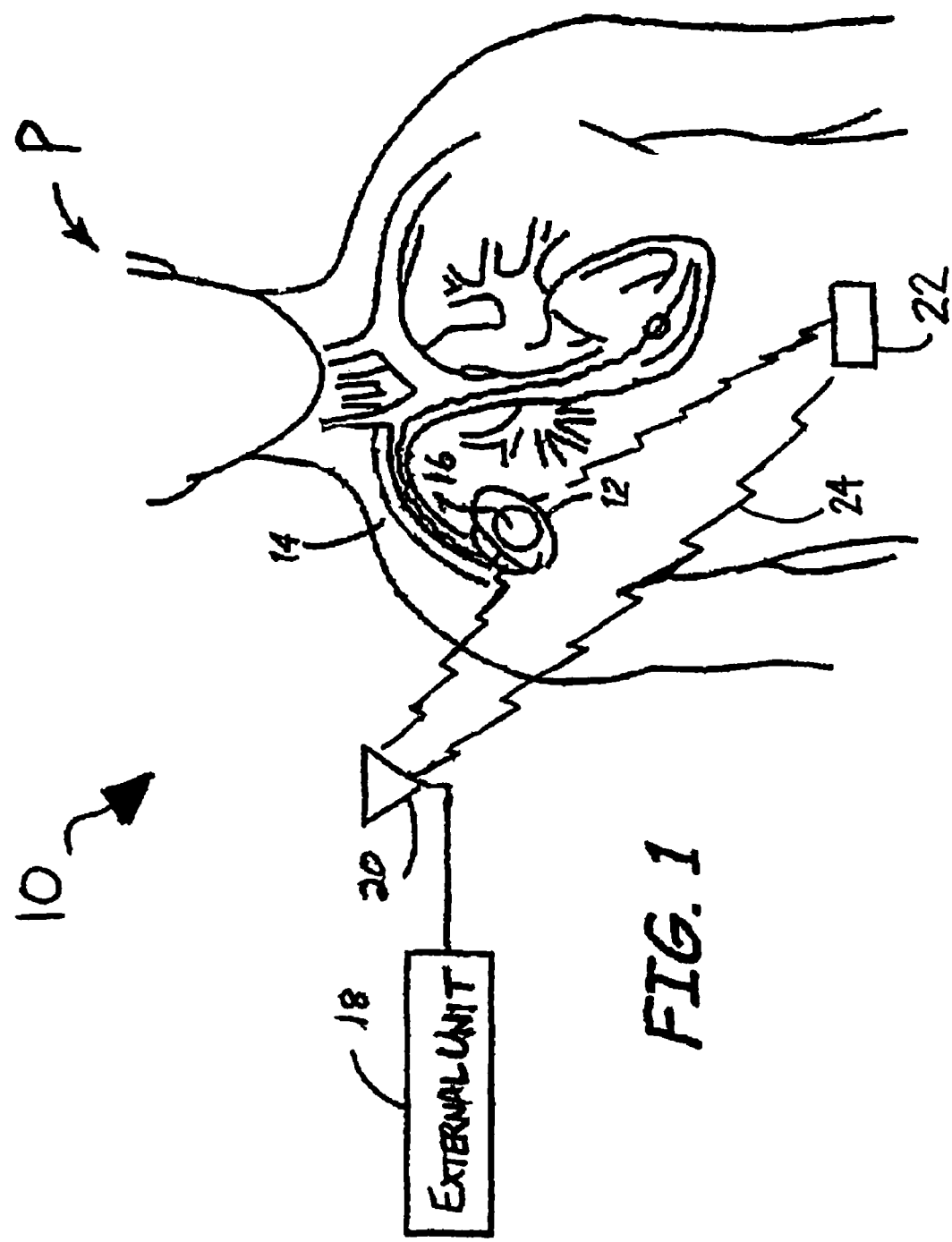
FIG. 1 is a schematic diagram illustrating a communication system for communicating medical data and other information between one or more medical devices and an external unit.

FIG. 1 is a schematic diagram illustrating communication system 10 for communication involving IMD 12, which includes lead 14 and antenna 16. IMD 12 has the capability to communicate with external unit 18 via antenna 20, and also with device 22 via communication link 24. In one embodiment, IMD 12 is an implantable cardioverter defibrillator (ICD), but the present invention is equally applicable to many types of medical devices, including both implantable medical devices and external medical devices. IMD 12 is capable of providing therapies and/or sensing physiological events of the heart of patient P via one or more leads 14. Antenna 16 is used to communicate with external unit 18 and with device 22, and may be any apparatus capable of sending or receiving electromagnetic waves, including for example a surface mounted antenna, an inductor, or a half-wave strip. Alternatively, antenna 16 may be configured only for communication with external unit 18, and a separate, independent antenna may be employed for communication with device 22.

External unit 18 is a device, such as a programmer, capable of bi-directional communication with IMD 12 via antenna 20. Antenna 20 may be any type of RF antenna capable of communicating in the desired RF frequencies with IMD 12, and may be located inside or outside of a housing of external unit 18.

Device 22, similar to IMD 12, is capable of providing therapies and/or sensing physiological events in the body of patient P. Device 22 may be any of a number of different devices, such as an insulin pump, a drug pump, a cardiac sensor, a neurological sensor, a glucose sensor, or another device (the location of device 22 shown in FIG. 1 is, of course, not representative of a typical implantation location of all of these types of devices). Additional devices (not shown) may be implanted in or otherwise associated with patient P as well, communicating with other devices in a manner similar to device 22.

Communication between IMD 12 and external unit 18, between IMD 12 and IMD 22, and between external unit 18 and IMD 22, can be performed over any communication band. In one embodiment, the communication occurs over a public radio frequency band. In another embodiment, the communication occurs over the Medical Implant Communication (MICs) band between 402 MHz and 405 MHz. Other frequency bands may also be used. Although the present invention is described with reference to radio frequency bands, it is recognized that the present invention is also useful with other types of electromagnetic communication.

Because IMD 12 and device 22 have finite battery capacity, an important consideration in the design of RF communication system 10 is the energy efficiency of IMD 12 and device 22. A substantial factor in the energy efficiency of IMD 12 and device 22 is the time that their transceivers spend either transmitting or receiving. Energy efficiency is less of an issue in the design of external unit 18, because external unit 18 is generally connected to an external power source such as a 120V AC. Therefore, methods of operating the transceivers of IMD 12 and device 22 that reduce the energy consumption of those components, even in exchange for additional energy consumption by the transceiver of external unit 18, are beneficial.

While transmitters only need to be turned on when there is something to transmit, receivers must be turned on much more frequently. No communication can take place unless the receiver is on, at least momentarily, to detect an attempted transmission. To provide a fast response time, a receiver may sample a communication channel as often as twice every second or more. But, a receiver that turns on just twice every second will turn on 172,800 times in one day. A transmitter, on the other hand, may turn on only a handful of times in that same period. Therefore, an improvement in the efficiency of use of a receiver can provide an increase in the effective life of the device.

External unit 18 assists in reducing the energy consumed by medical device receivers by transmitting a preamble signal (sometimes referred to as a "wake-up" signal) prior to the transmission of data. This use of a preamble signal allows the device receivers to sample the communication channel(s) periodically, rather than having to remain on at all times, while still ensuring that the transmission of any data will not be missed. The preamble signal contains a modulation pattern known by the device receivers. If the receivers detect energy on a communication band, but find that it does not contain the known modulation pattern, the receivers can shut down knowing that the detected energy is not a communication initiated by external unit 18 for its benefit. Furthermore, the preamble signal may contain embedded data which further improves the energy efficiency of the device receivers. This data informs the receivers of information pertinent to the communication link (such as channel information and communication mode) for the subsequent transmission of data. The receivers may continue operating in a low power mode while receiving the embedded data, and then adjust their configuration settings as specified by the embedded data to initiate the higher power receiver mode for receipt of the transmitted data. Further discussion of the embedding of data in the preamble signal may be found in the aforementioned U.S. application Ser. No. 11/224,595.

Figure 2A:
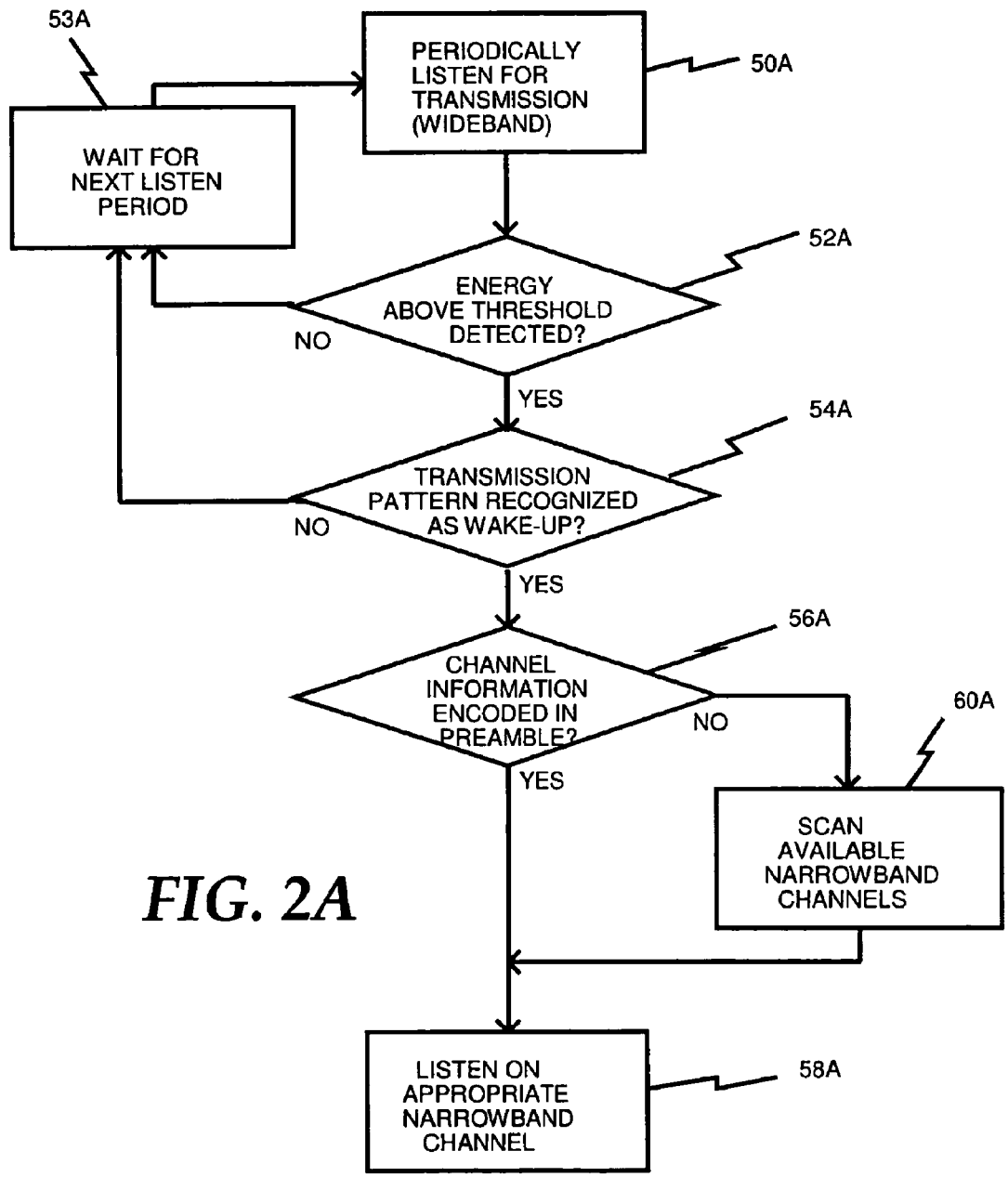
FIG. 2A is a flow diagram illustrating a first example of the operation of receivers to detect a wake-up signal.

FIG. 2A is a flow diagram illustrating a first example of the operation of receivers to detect a wake-up signal. A device receiver periodically operated to listen for a transmission in order to detect the existence of a transmission, as indicated by box 50A. This initial listening operation is performed by a wideband receiver. The wideband receiver is operated to detect whether transmission energy above a threshold on any channel of a selected group of channels is occurring, as indicated by decision box 52A. If energy above the threshold is not detected, the receiver can turn off until the next listening period, as indicated by box 53A. If energy above the threshold is detected, the receiver remains on to attempt to identify a transmission pattern associated with the detected energy that matches the pattern of a wake-up signal, as indicated by decision box 54A. If the transmission pattern corresponds to a wake-up signal, the receiver will then switch to a narrowband receiving mode. If channel information is encoded in the wake-up signal (decision box 56A), then the receiver will switch to the appropriate channel based on that information, as indicated by box 58A. If channel information is not encoded in the wake-up signal, the receiver performs a scan of the available channels, as indicated by box 60A, and determines which channel contains the wake-up signal transmission. Once the correct channel is determined, the receiver switches to the appropriate channel, as indicated by box 58A. After the receiver has switched to the appropriate channel, data can be received on the channel in the customary manner. Further discussion of a wake-up procedure of this kind can be found in the aforementioned U.S. application Ser. No. 11/224,593.

Figure 2B:
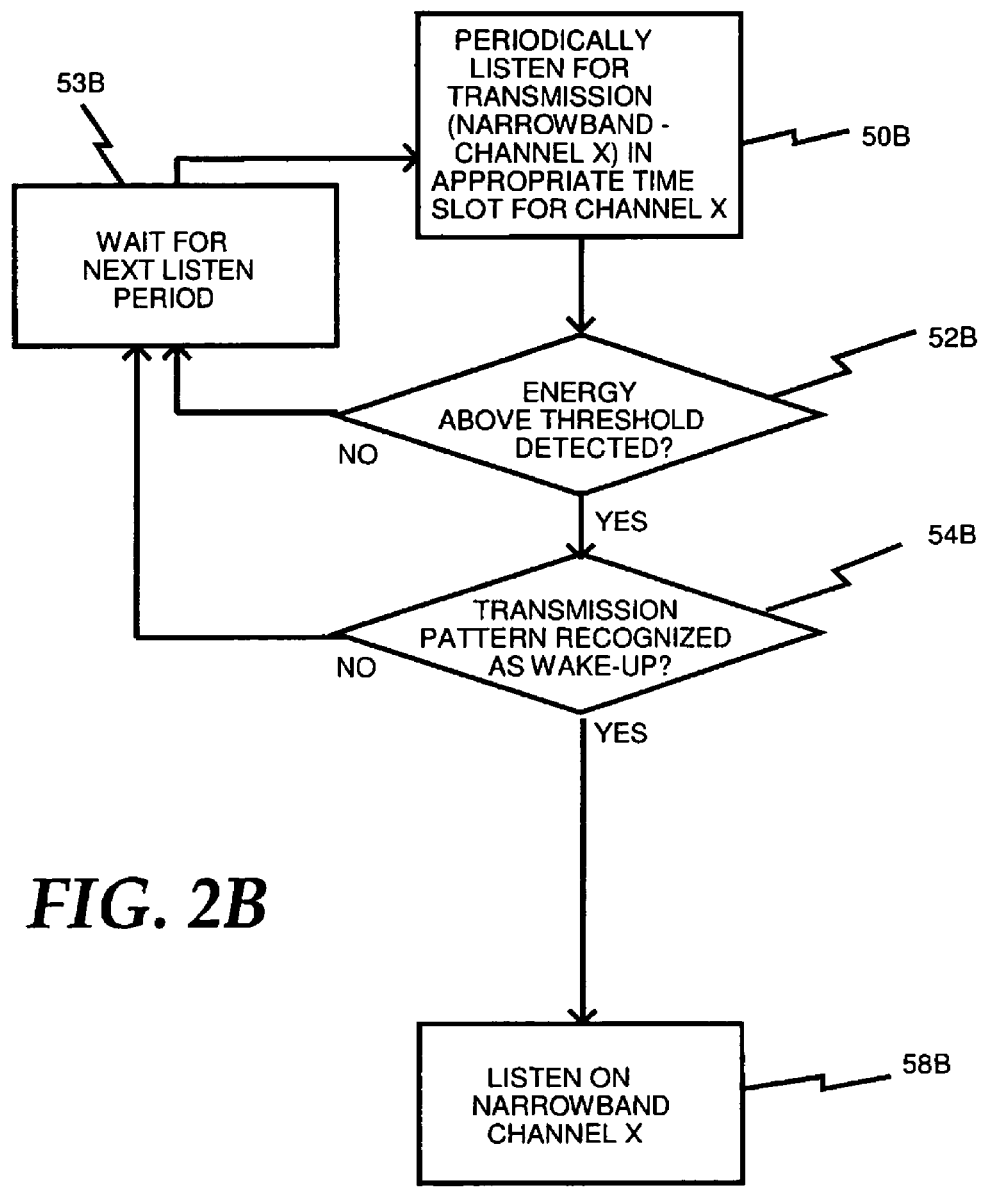
FIG. 2B is a flow diagram illustrating a second example of the operation of receivers to detect a wake-up signal.

FIG. 2B is a flow diagram illustrating a second example of the operation of receivers to detect a wake-up signal. A device receiver is periodically operated to listen for a transmission in order to detect the existence of a transmission, as indicated by box 50B. This initial listening operation is performed by a narrowband receiver (unlike the wideband listening example described above with respect to FIG. 2A) operating on a channel designated as "channel X." In a synchronous communication system, each channel (such as channel X) has an assigned time slot, and the narrowband receiver listens for a transmission in the time slot that is assigned to channel X. The narrowband receiver is operated to detect whether transmission energy above a threshold on channel X is occurring, as indicated by decision box 52B. If energy above the threshold is not detected, the receiver can turn off until the next listening period, as indicated by box 53B. If energy above the threshold is detected, the receiver remains on to attempt to identify a transmission pattern associated with the detected energy that matches the pattern of a wake-up signal, as indicated by decision box 54B. If the transmission pattern corresponds to a wake-up signal, the receiver listens for data on channel X in the customary manner, as indicated by box 58B.

Figure 2C:
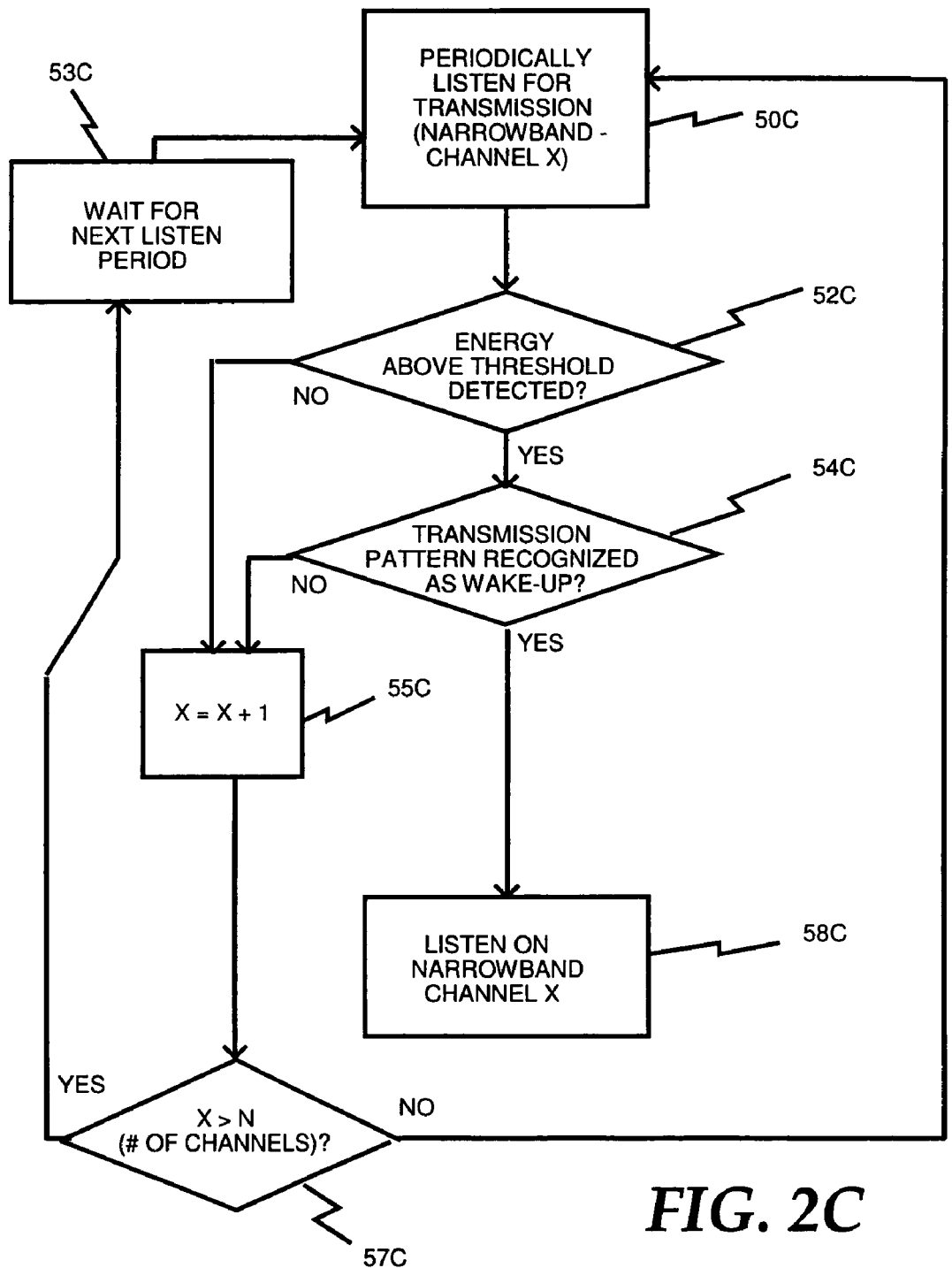
FIG. 2C is a flow diagram illustrating a third example of the operation of receivers to detect a wake-up signal.

FIG. 2C is a flow diagram illustrating a third example of the operation of receivers to detect a wake-up signal. A device receiver is periodically operated to listen for a transmission in order to detect the existence of a transmission, as indicated by box 50C. This initial listening operation is performed by a narrowband receiver (unlike the wideband listening example described above with respect to FIG. 2A) operating on a channel designated a synchronous communication system, each channel in a synchronous communication system (such as channel X) has an assigned time slot, and the narrowband receiver listens for a transmission in the time slot that is assigned to channel X. The primary difference between the example shown in FIG. 2C and the example described above with respect to FIG. 2B is that the FIG. 2C example listens to all available channels to attempt to detect a transmission. The narrowband receiver is operated to detect whether transmission energy above a threshold on channel X is occurring, as indicated by decision box 52C. If energy above the threshold is not detected, then the channel number is incremented as indicated by box 55C, and a determination is made as to whether all available channels have been checked, as indicated by box 57C. If all channels have been checked and no transmission has been detected, the receiver can turn off until the next listening period, as indicated by box 53C. If there are channels remaining to be checked, the process repeats at box 50C. If energy above the threshold is detected (box 52C) and a transmission pattern associated with the detected energy matches the pattern of a wake-up signal (box 54C), then the receiver listens for data on channel X in the customary manner, as indicated by box 58C.

Figure 2D:
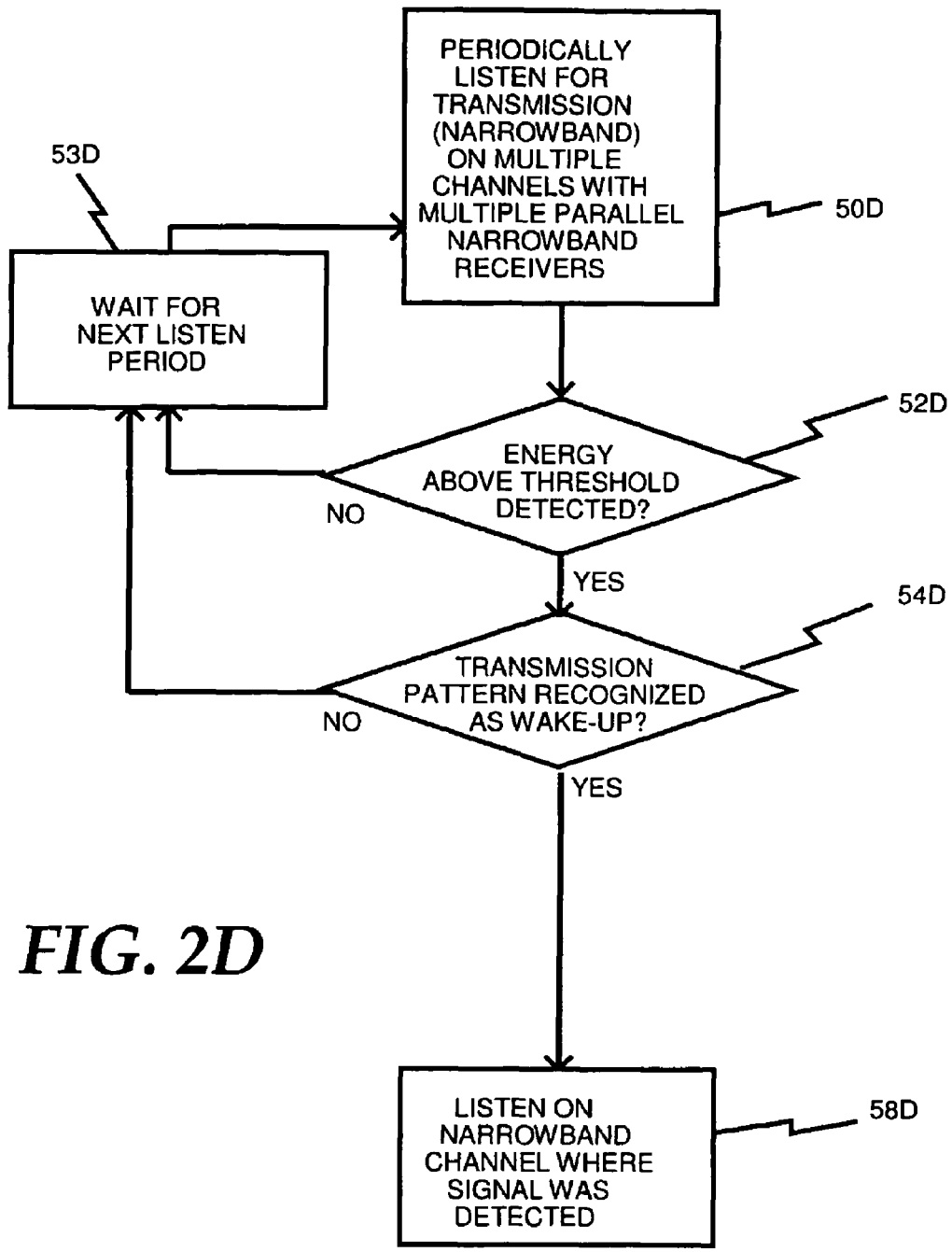
FIG. 2D is a flow diagram illustrating a fourth example of the operation of receivers to detect a wake-up signal.

FIG. 2D is a flow diagram illustrating a fourth example of the operation of receivers to detect a wake-up signal. Multiple device receivers are periodically operated in parallel to listen for a transmission on multiple channels in order to detect the existence of a transmission, as indicated by box 50D. As discussed above, each channel in a synchronous communication system has an assigned time slot, and the narrowband receivers listen for transmissions in the time slots that are assigned to the active channels of the narrowband receivers. The narrowband receivers are operated to detect whether transmission energy above a threshold on the active channels is occurring, as indicated by decision box 52D. If energy above the threshold is not detected, the receiver can turn off until the next listening period, as indicated by box 53D. If energy above the threshold is detected, the receiver that detected the energy remains on to attempt to identify a transmission pattern associated with the detected energy that matches the pattern of a wake-up signal, as indicated by decision box 54D. If the transmission pattern corresponds to a wake-up signal, the receiver listens for data on the channel where the signal was detected in the customary manner, as indicated by box 58D.

Figure 3:
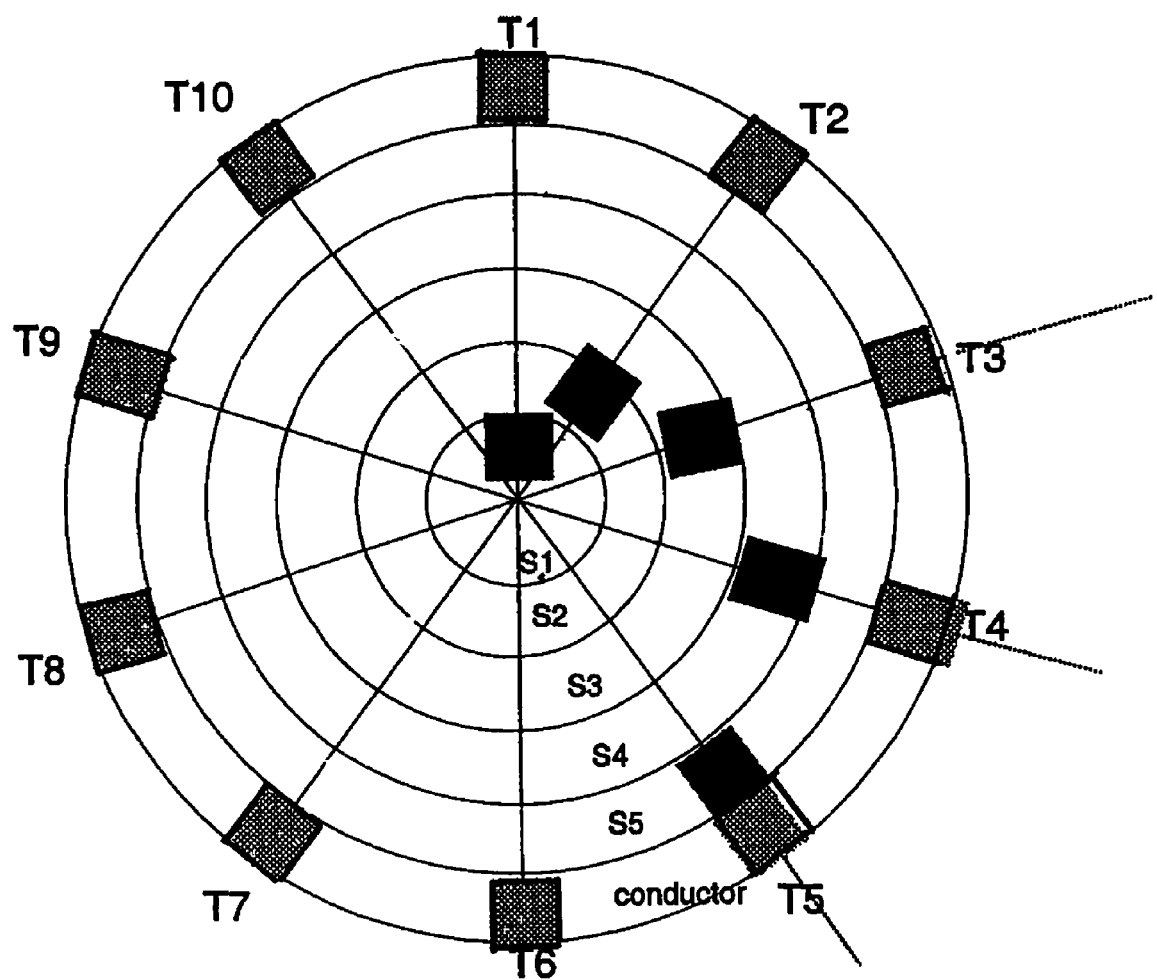
FIG. 3 is a diagram illustrating the timing of synchronous communication in a communication system.

In order to ensure that the transceivers of IMD 12 and device 22 are operated in an efficient manner that minimizes battery usage, while enabling advanced communication of data with each other and/or with external unit 18, a communication protocol is employed. In a first embodiment, a synchronous communication protocol is employed. FIG. 3 is a diagram illustrating the timing of such a synchronous communication protocol. The diagram of FIG. 3 is applicable to a relatively complex communication system, which includes IMD 12 (labeled "conductor" in FIG. 3), device 22 (labeled sensor S1 in FIG. 3), and four additional sensors (not shown in FIG. 1, labeled sensors S2, S3, S4 and S5 in FIG. 3) that are either internal or external to the body. Together, these devices make up a local body area network (LBAN) of devices that are able to communicate with one another. In this embodiment, all of the devices include transmitters and receivers. The relatively high number of sensors is included in FIG. 3 to provide a clear illustration of the features of the synchronous communication protocol.

The synchronous communication protocol illustrated in FIG. 3 makes use of a plurality of assigned time slots for communication. One device of the network operates as the conductor to implement the communication protocol. In the example shown in FIG. 3, IMD 12 operates as the conductor. The device selected to be the conductor may be determined in a number of ways, such as by predetermined assignment, by a hierarchical rank assigned to the devices of the network, by processing capability, by battery capability, or by other means. The conductor device establishes a communication cycle that is divided into a plurality of time slots assigned to the constituents of the network, shown in FIG. 3 as time slots T1-T10. In one embodiment, each time slot T1-T10 has a duration of 0.5 seconds. The conductor device then operates its receiver to listen for transmissions from the sensors S1-S5 in each time slot. Sensors S1-S5 operate their receivers to listen for transmissions only in the appropriately assigned time slot. Also, when sensors S1-S5 need to send data to the conductor device, they operate their transmitters to initiate a transmission in the appropriately assigned time slot. The conductor device listens for these transmissions, receives the data, and responds to complete the communication session with the transmitting sensor. As a result of this synchronous communication protocol, each sensor can turn its transmitter and receiver off during all time slots that are not assigned to that particular sensor, reducing the battery usage of those sensors. In the example shown in FIG. 3, time slots T6-T10 are reserved for future devices that may join the network.

In many embodiments, sensors S1-S5 communicate with the conductor device on different frequencies (channels), as well as in different time slots. The appropriate communication frequency may be established by predetermined assignment to particular devices, or may be dynamically determined for each transmission based on factors such as channel interference, noise, or others. The receiving device (e.g., the conductor device) may detect the frequency at which communication is occurring according to the method described above in FIG. 2A, for example.

In some embodiments, time slots T1-T10 are not rigidly assigned to individual constituents of the network. In one example, time slots T1-T10 are each assigned to a different channel frequency, but are available for communication by any constituent of the network. In this case, a network constituent performs a listen-before-talk (LBT) routine to ensure that a channel is clear, and then transmits a wake-up signal pattern and data on the appropriate channel (and in the appropriate time slot). In another example, all channels may be monitored during each time slot, so that any channel could be used in any time slot if the channel is clear. Other variations of these schemes are also possible.

One factor of the synchronous communication protocol that must be accounted for is the possibility of drift between the internal clocks of the conductor device and sensors S1-S5. Over long periods of inactivity, the clocks of the conductor device and sensor devices S1-S5 have the potential to become desynchronized with one another because of drifting of the devices' internal clocks. For example, if the internal clocks are accurate to 1 part-per-million (ppm), the clocks will drift up to 60 micro-seconds (μs) per minute, or 3.6 milli-seconds (ms) per hour. As a result, in order to stay synchronized, sensors S1-S5 transmit a signal (such as a signal that mimics the wake-up signal used by the system) in advance of the time slot in which they have been assigned to transmit, to account for the possibility of clock drift. The wake-up signal continues for a time period that extends beyond the beginning of the time slot by a time that accounts for the possibility of clock drift in the opposite direction. In the example given above, sensors S1-S5 would each transmit a wake-up signal that begins 3.6 ms before the assigned time slot begins, and ends 3.6 ms after the beginning of the assigned time slot. This time period before and after the beginning of the assigned time slot is referred to as a "drift window," as the window is utilized to account for the possibility of clock drift.

If sensors S1-S5 do not have data to transmit, they will simply transmit the wake-up signal periodically (such as once an hour, for example) to resynchronize their clocks. If sensors S1-S5 do have data to transmit, the wake-up signal is transmitted first (in the assigned time slot), spanning the drift window, to ensure that the transmission is detected. The receiving device typically needs additional time following transmission of the wake-up signal to identify the wake-up signal pattern and determine the appropriate channel for communication. The transmitting sensor waits long enough for the receiving device to make these determinations before transmitting the actual data payload.

In one embodiment, the conductor device transmits information relating to the identity and status of all constituents of the network (including information pertaining to the assignment of other constituents' time slots) to each device/sensor. This information allows the devices of the network to communicate with each other directly. A transmitting sensor transmits a wake-up signal in the receiving sensor's assigned time slot in order to effect this communication. In this situation, the drift window may be twice as large as the drift window described above with respect to communication between the conductor and sensors S1-S5, and the transmitting sensor times its wake-up signal transmission accordingly.

In some communication networks involving implantable and/or external medical devices, sensors (or other devices) may be employed that have no ability to receive communications. Other sensors may be employed that have very limited ability to receive communications, operating most of the time in a mode that lacks the ability to receive communications (due to limited battery capacity, limited processing capability, or both, for example). In these types of systems, a modified communication protocol is employed to accommodate these types of sensors.

Figure 4:
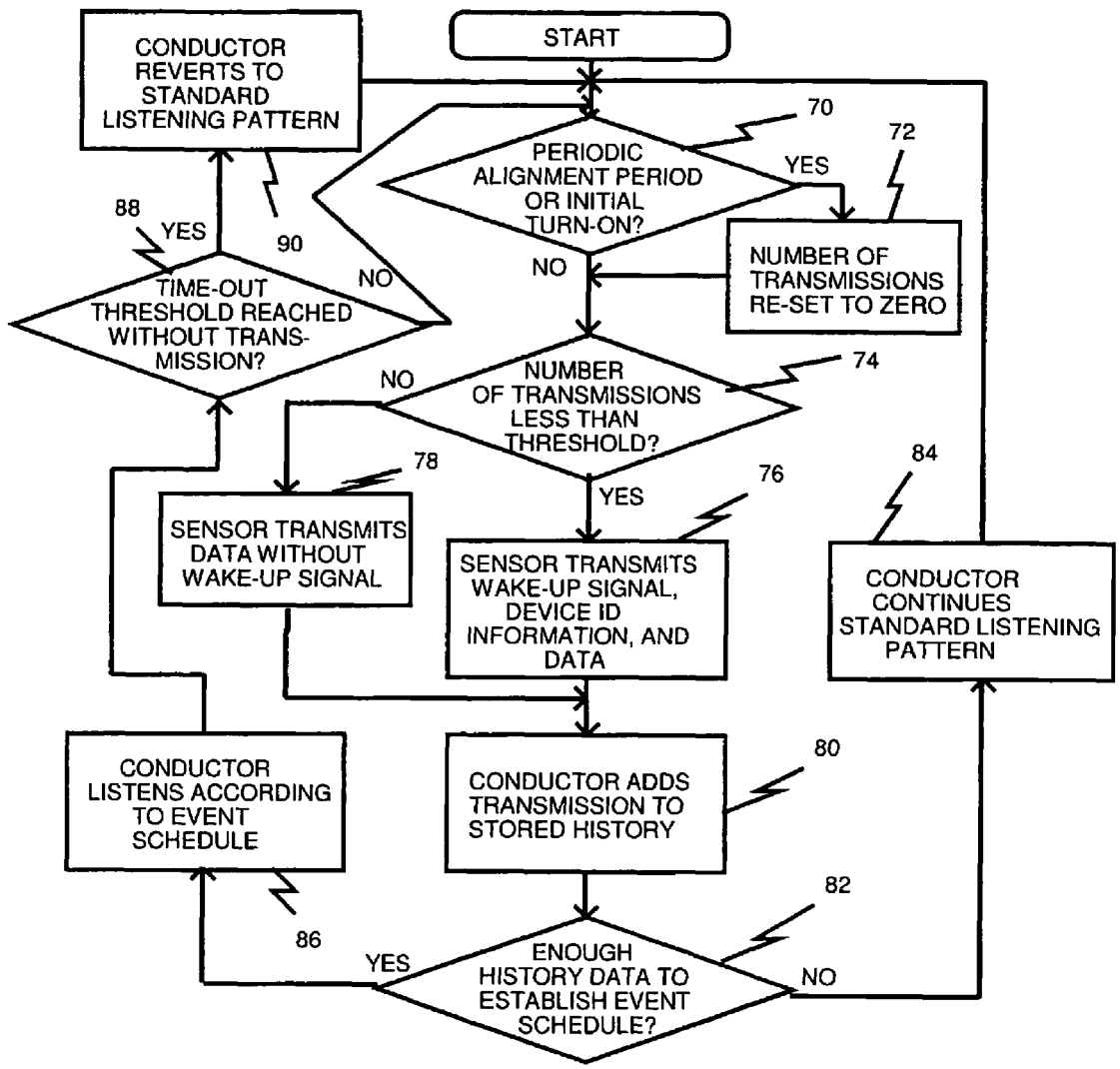
FIG. 4 is a flow diagram illustrating a protocol for communication that involves sensors without receiver capability.

FIG. 4 is a flow diagram illustrating a protocol for communication that involves sensors without receiver capability. When the sensor is initially activated, or periodically after initial activation (such as once per hour, for example), an alignment procedure is performed. This is illustrated by decision box 70, showing that the protocol resets the number of transmissions counted by the sensor to zero (box 72) at sensor initialization or at commencement of a periodic alignment period. Next, the counted number of transmissions that have been performed since sensor initialization or commencement of the alignment period is compared to a threshold at decision box 74. This comparison is made so that the sensor transmits a full wake-up signal, including device ID information, along with its data for a first number of transmissions (box 76) that enables the conductor device of the network to receive the information despite the fact that transmissions from this particular sensor may not yet have been scheduled or assigned to a time slot. The wake-up signal is long enough to ensure that the conductor device can receive and decode the signal to identify the signal as a wake-up signal. If enough transmissions have already been sent by the sensor (greater than the threshold), then it is assumed that the conductor of the network has been able to establish an event schedule of some kind and no longer needs the wake-up signal to precede transmission of data, so data is sent without a wake-up signal (box 78).

After the sensor has transmitted its data, the conductor adds the information related to the transmission to a transmission history record, as indicated by box 80. The conductor then determines whether there is enough history data to establish an event schedule which predicts the timing of future transmissions from the particular sensor (decision box 82). In one embodiment, the existence of sufficient history data to establish an event schedule corresponds to the threshold number of transmissions beyond which the sensor ceases transmitting wake-up signals before transmitting data.

If there is insufficient history data to establish an event schedule, the conductor device continues to operate its receiver according to a standard listening pattern, as indicated by box 84. However, if there is enough data to establish an event schedule (or if an event schedule had already been established), the conductor device listens for transmissions from the sensor in accordance with the event schedule, as indicated by box 86. In a system that employs a synchronous communication protocol as shown in FIG. 3, the establishment of the event schedule is similar to the assignment of a time slot for each sensor in the network, and the conductor device adds the event schedule information to its map of assigned time slots and network devices.

It is possible for the sensor to lose communication with the conductor device, such as by moving out of communication range or desynchronization due to clock drift, for example. To account for this possibility, a time-out threshold can be established, and if the time-out threshold is exceeded (decision box 88), the conductor device can revert back to its standard listening pattern (box 90) so that the time assigned to listen for transmissions from the sensor is not wasted for the time until the next periodic realignment occurs.

As mentioned above, the protocol shown in FIG. 4 is suitable for use with the synchronous timing scheme shown in FIG. 3. The protocol of FIG. 4 allows synchronous communication to be performed even with devices that do not include a receiver and therefore cannot receive time slot assignments. The conductor device of the network utilizes its processing capability to schedule the time slot assignments for the other constituents of the network in a manner that does not interfere with the transmissions made by sensors that do not possess receiving capability (and therefore cannot adjust transmission timing based on instructions from the conductor device). In typical embodiments, sensors that do not have receiving capability are configured to transmit with fixed, predetermined timing, so that event scheduling for predicted future transmissions is relatively accurate.

Figure 5:
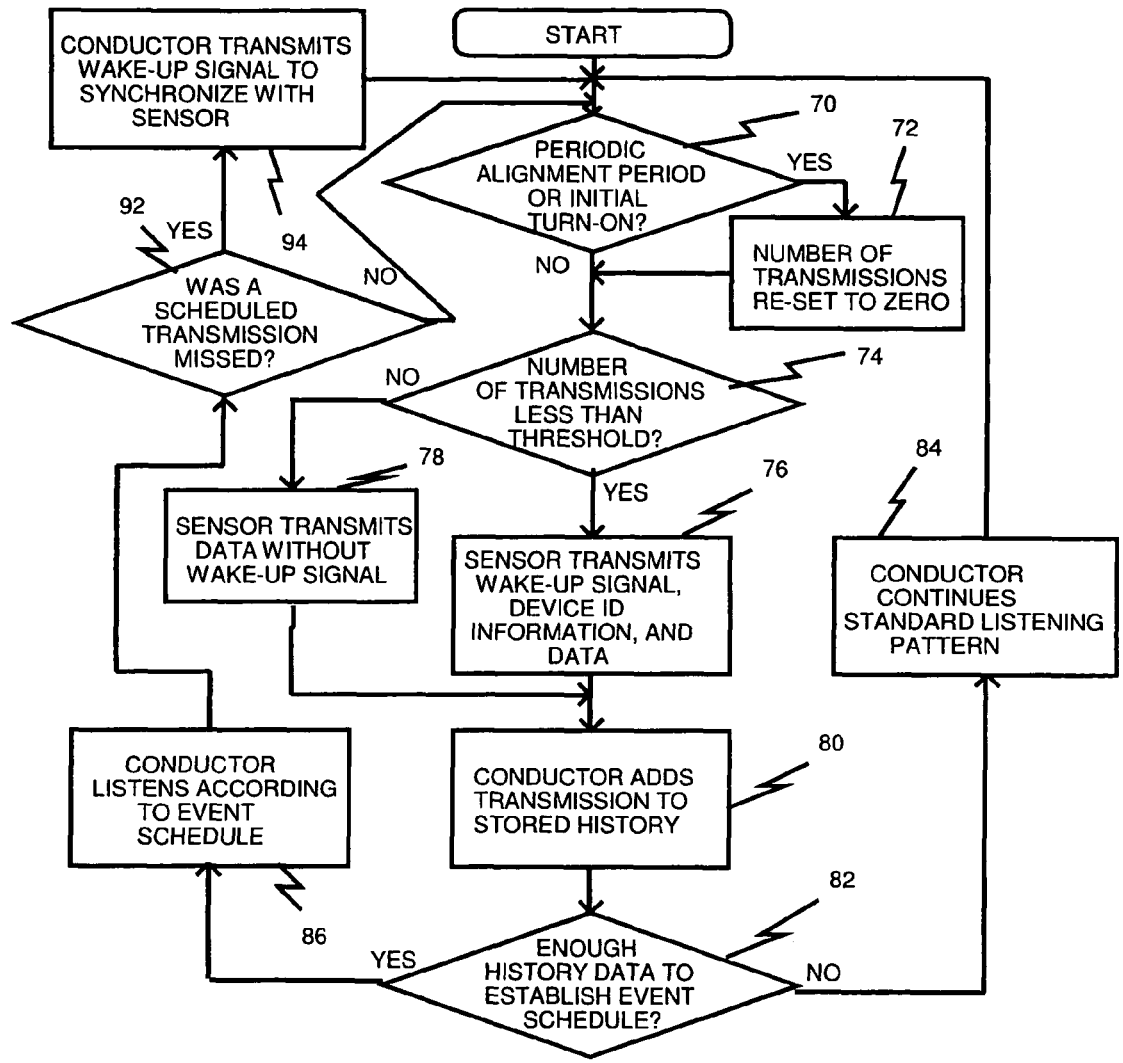
FIG. 5 is a flow diagram illustrating a protocol for communication that involves sensors having limited receiver capability.

In systems that include sensors with limited receiving capability (i.e., a receiver that is operated only at relatively infrequent intervals), the protocol of FIG. 4 can be modified slightly to utilize this capability to maintain synchronization between periodic alignment periods. This modified protocol is shown in FIG. 5. The protocol in FIG. 6 is the same as that shown in FIG. 4, except that the time-out threshold procedure that accounts for communication loss (decision box 88 and box 90 of FIG. 4) is replaced by a procedure for resynchronizing the sensor with the conductor device. Specifically, as the conductor device listens for transmissions according to an established event schedule at box 86, the conductor determines whether a transmission on the event schedule has been missed (decision box 92). If a transmission has been missed (or if a number of transmissions greater than a threshold number have been missed), the conductor device transmits a wake-up signal for a time that is at least as long as the scan time of the receiver associated with the sensor, as indicated by box 94. One example of the receiver scan time for a limited receiving capability sensor is five seconds. This resynchronization procedure blocks communications on the network and awakens all of the sensors in the network, and therefore the conductor device may be configured to use this procedure sparingly, or possibly

What is claimed is:

1. A method of communicating information between constituents of a network that includes at least one medical device, the method comprising:
   establishing a first constituent of the network as a conductor;
   assigning time slots to each constituent of the network other than the conductor; and
   communicating information between the constituents of the network, including between the conductor and the other constituents, and between the other constituents, in the assigned time slots.

2. The method of claim 1, wherein establishing the first constituent of the network as the conductor is performed by evaluating hierarchical ranks associated with each constituent of the network.

3. The method of claim 1, wherein establishing a first constituent of the network as the conductor is performed by evaluating capabilities of each constituent of the network.

4. The method of claim 1, wherein communicating information between the conductor and the other constituents of the network in the assigned time slots comprises:
periodically communicating a wake-up signal that spans a drift window time period around the assigned time slots to resynchronize the conductor with the constituents of the network.

5. The method of claim 1, wherein the conductor transmits information relating to an identity and status of all constituents of the network to each constituent of the network.

6. The method of claim 5, wherein communicating information between a transmitting constituent and a receiving constituent of the network, neither one of which being the conductor, comprises:
transmitting a wake-up signal from the transmitting constituent during a time slot assigned to the receiving constituent, the wake-up signal spanning a drift window time period around the time slot to resynchronize the transmitting constituent with the receiving constituent.

7. The method of claim 1, wherein the time slots assigned to each of the constituents of the network each have a different frequency associated therewith.

8. The method of claim 1, wherein communicating information between the constituents of the network comprises:
dynamically determining a frequency for communication.

9. The method of claim 1, wherein assigning time slots to each constituent of the network other than the conductor comprises:
operating at least one constituent of the network other than the conductor to transmit a wake-up signal with its data to the conductor to identify the constituent;
establishing an event schedule which includes time slots assigned to predict the timing of future transmissions from the constituent based on a history of transmissions from the constituent; and
operating the conductor to listen for transmissions from the constituent in the time slots established by the event schedule.

10. The method of claim 9, wherein the conductor reverts away from the event schedule and back to a standard listening pattern following a lack of received transmissions from the constituent for a time period that exceeds a threshold time-out period.

11. The method of claim 9, wherein the conductor resynchronizes with the constituent if a number of scheduled transmissions from the constituent greater than a threshold are not received by the conductor.

12. A wireless network for communicating medical data among a plurality of devices, comprising:
a plurality of constituent devices capable of wirelessly transmitting medical data; and
one of the constituent devices configured as a conductor device to assign a time slot to each of the other constituent devices for transmission,
wherein the constituent devices are configured to communicate medical data between each other, including between the conductor device and the other constituent devices, and between the other constituent devices, in the assigned time slots.

13. The wireless network of claim 12, wherein the conductor device is determined by evaluating hierarchical ranks associated with devices of the network.

14. The wireless network of claim 12, wherein the conductor device is determined by evaluating capabilities of each device in the network.

15. The wireless network of claim 12, wherein the constituent devices periodically transmit a wake-up signal that spans a drift window time period around their assigned time slot to resynchronize the constituent devices with the conductor.

16. The wireless network of claim 12, wherein the conductor transmits information relating to an identity and status of all constituent devices of the network to each constituent device of the network.

17. The wireless network of claim 16, wherein each of the constituent devices is operable to transmit a wake-up signal to a receiving constituent device during a time slot assigned to the receiving constituent device, the wake-up signal spanning a drift window time period around the time slot assigned to the receiving constituent device to resynchronize the constituent device with the receiving constituent device.

18. The wireless network of claim 12, wherein each of the constituent devices is operable to transmit a wake-up signal to the conductor along with the medical data to be transmitted to identify the constituent device, and wherein the conductor device establishes an event schedule that includes time slots assigned to predict the timing of future transmissions from the constituent device based on a history of transmissions from the constituent device.

19. The wireless network of claim 18, wherein the conductor device reverts away from the event schedule and back to a standard listening pattern following a lack of received transmissions from the constituent device for a time period that exceeds a threshold time-out period.

20. The wireless network of claim 18, wherein the conductor device resynchronizes with the constituent device if a number of scheduled transmissions from the constituent device greater than a threshold are not received by the conductor.

* * * * *